(12) United States Patent
Silk

(10) Patent No.: US 7,648,441 B2
(45) Date of Patent: Jan. 19, 2010

(54) SELF-CONTAINED REAL-TIME GAIT THERAPY DEVICE

(76) Inventor: Jeffrey E. Silk, P.O. Box 533, Orem, UT (US) 84059

( * ) Notice: Subject to any disclaimer, the term of this patent is extended or adjusted under 35 U.S.C. 154(b) by 773 days.

(21) Appl. No.: 10/986,557

(22) Filed: Nov. 10, 2004

(65) Prior Publication Data

US 2006/0100546 A1     May 11, 2006

(51) Int. Cl.
*A63B 15/02* (2006.01)
(52) U.S. Cl. .................. 482/1; 482/8; 482/9; 482/900; 600/587; 702/160
(58) Field of Classification Search ............... 482/1–9, 482/51, 54, 74, 900–902; 434/247; 600/481, 600/546, 587, 595, 592; 702/160
See application file for complete search history.

(56) References Cited

U.S. PATENT DOCUMENTS

| | | | | |
|---|---|---|---|---|
| 4,191,949 A | | 3/1980 | Myers | 340/573.7 |
| 4,557,275 A | | 12/1985 | Dempsey, Jr. | 600/595 |
| 4,566,461 A | * | 1/1986 | Lubell et al. | 600/481 |
| 4,763,287 A | * | 8/1988 | Gerhaeuser et al. | 702/160 |
| 4,771,394 A | * | 9/1988 | Cavanagh | 702/160 |
| 4,814,661 A | * | 3/1989 | Ratzlaff et al. | 310/328 |
| 4,858,620 A | | 8/1989 | Sugarman et al. | 600/587 |
| 4,938,476 A | | 7/1990 | Brunelle et al. | 482/148 |
| 5,269,081 A | | 12/1993 | Gray | 36/136 |
| 5,337,758 A | | 8/1994 | Moore et al. | 600/594 |
| 5,433,201 A | | 7/1995 | Manthey | 600/595 |
| 5,485,402 A | | 1/1996 | Smith et al. | 364/566 |
| 5,511,561 A | | 4/1996 | Wanderman et al. | 600/592 |
| 5,775,332 A | * | 7/1998 | Goldman | 600/587 |
| 5,957,870 A | * | 9/1999 | Yamato et al. | 600/592 |
| 6,010,465 A | * | 1/2000 | Nashner | 600/595 |
| 6,234,982 B1 | * | 5/2001 | Aruin | 600/595 |
| 6,298,314 B1 | * | 10/2001 | Blackadar et al. | 702/178 |
| 6,356,856 B1 | * | 3/2002 | Damen et al. | 702/160 |
| 6,645,126 B1 | * | 11/2003 | Martin et al. | 482/54 |
| 6,678,549 B2 | | 1/2004 | Cusimano et al. | 600/546 |
| 6,692,449 B1 | | 2/2004 | Brown | 600/595 |
| 6,765,726 B2 | | 7/2004 | French et al. | 259/630 |
| 6,788,976 B2 | | 9/2004 | Gesotti | 607/49 |
| 6,882,955 B1 | * | 4/2005 | Ohlenbusch et al. | 702/160 |
| 7,353,137 B2 | * | 4/2008 | Vock et al. | 702/173 |
| 2005/0277844 A1 | * | 12/2005 | Strother et al. | 600/546 |

(Continued)

OTHER PUBLICATIONS

B&L Engineering *Stride Analyzer Product Information* and Stride Analyzer Manual, Chapters 1-2 and Appendices A-C, 2004.

(Continued)

*Primary Examiner*—Glenn Richaman
(74) *Attorney, Agent, or Firm*—J. David Nelson

(57) ABSTRACT

A self-contained, real-time self-use gait therapy device with a gait sensor, actuator, output speaker, and battery receptacle enclosed in a component case with a belt clip. Based upon step duration, step impact force, or step form data generated by the gait sensor, the actuator drives the speaker, producing beeps on a real-time basis with the pitch of each beep being a function of the step duration, step impact force, or step form for each step of the user. The speaker output is monitored and used by the user on a real-time basis to modify and improve his or her gait.

25 Claims, 2 Drawing Sheets

U.S. PATENT DOCUMENTS

2007/0068244 A1* 3/2007 Billing et al. .................. 73/172

OTHER PUBLICATIONS

IDEEA Company, *Portable Gait Lab*, 2004.

Andrew L. McDonough et al. *The Validity and Reliability of the GAITRite Systems. Measurements: A Preliminary Evaluation*, Arch Phys Med Rehabil vol. 82, Mar. 2001.

* cited by examiner

SELF-CONTAINED REAL-TIME GAIT THERAPY DEVICE

FIELD OF THE INVENTION

This invention is in the field of lower extremity physical therapy assist devices and in particular is in the field of gait therapy devices providing gait monitoring and real-time feedback for gait modification and correction.

BACKGROUND OF THE INVENTION

Congenital deficit, injury or illness involving one or more lower extremities or the spine or torso can result in the advent of a gait irregularity. Generally an irregularity is the manifestation of an asymmetry in the movement or step pattern of the right and left legs. A gait irregularity can include a step duration, step force, or step form difference between the left leg step and the right leg step. Anatomically, the irregularity can be the result of injury, atrophy, denervation or impaired nervation of one or more muscles or muscle groups, ligament or tendon injury, joint injury or disease, or pain or stiffness of any kind involving the lower extremities, spine or lower torso. An irregularity in the step duration, step force, or step form is commonly referred to as a limp.

Not only is elimination or reduction of gait irregularity an important part of the therapeutic and healing process, it is often essential to prevent the further injury or chronic pain which can be caused by the abnormal stress placed on the body as a result of gait irregularities.

A number of devices are disclosed in the art for gait monitoring or therapy.

U.S. Pat. No. 6,234,982 to Aruin discloses a device which provides for feedback training by the user by providing a signal in response to the change in distance between the legs of the user or between the body of the user and an assistive device.

U.S. Pat. No. 5,485,402 to Smith et al discloses a monitor device which determines and records the number of steps taken by the user during selected intervals. The data is analyzed by a stand-alone computer and reports are generated.

U.S. Pat. No. 6,692,449 to Brown discloses an apparatus and method for sensing and measuring lower extremity position acuity during ongoing movement.

U.S. Pat. No. 6,645,126 to Martin et al discloses a device appended to a treadmill for aiding rehabilitation by varying the belt speed of the treadmill to match the step cycle of the user based upon the leg length or step length of the user.

U.S. Pat. No. 4,557,275 to Dempsey discloses a biofeedback system which uses switches positioned on the patient's body to respond to changes in orientation or position of a body member.

U.S. Pat. No. 5,511,561 to Wanderman et al discloses a device for monitoring the amount of force translated through a patent's heel in each gait cycle and providing an annunciated warning to the user when a pre-selected force limit is exceeded.

U.S. Pat. No. 5,269,081 to Gray discloses a shoe like device for monitoring the force being applied to a user's leg with each step and warning the user if a pre-selected force limit is exceeded.

U.S. Pat. No. 4,858,620 to Sugarman et al discloses a warning system which uses pressure sensors for monitoring the force being applied to an injured part of a user body and warning the user if a pre-selected force limit is exceeded.

U.S. Pat. No. 6,788,976 to Gesotti discloses a movement timing stimulator which provides sensory output to the user when the user's movement timing for particular part of the body, as with a neurological disorder such as Parkinson's disease, exhibits impaired movement.

U.S. Pat. No. 6,678,549 to Cusimano et al discloses a monitoring system for monitoring functional capacity of selected parts of the body of a person.

Devices for monitoring and recording gait characteristics data which are commercially available include the Stride Analyzer™ offered by B&L Engineering, the Life Gait System™ offered by IDEEA Co., and the Gaitrite System™ offered by CIR Systems Inc.

It is an object of the present invention to provide a gait therapy device which is economical, reliable and simple to use.

It is a further object of the present invention to provide a gait therapy device which is self-operated by the user.

It is a further objective of the present invention to provide a gait therapy device which provides real-time monitoring and feedback to allow real-time gait irregularity correction by the user.

It is a further object of the present invention to provide a gait therapy device which is self-contained and easily attaches to the body or clothing of the user.

It is a further object of the present invention to provide a gait therapy device which is readily adaptable to peripheral output and data download.

SUMMARY OF THE INVENTION

The self-contained, real-time gait therapy device of the present invention is intended to provide the user with real-time feedback that the user can self use on a real-time basis to attempt to remedy gait irregularities. However, it can be equipped with data storage and download capabilities for use by health care providers for evaluation and treatment. Regardless of the cause of gait irregularity, whether it be injury, medical intervention or other cause, an improper gait is generally undesirable and carries the potential for causing further medical problems, disabilities, decreased exercise and athletic performance, and chronic pain.

A basic embodiment of the present invention is comprised of a gait sensor, an actuator, an output element, a power supply and a component case. The gait sensor is preferably comprised of one or more sensing devices known to persons skilled in the art. The sensing devices that can be used include a weighted pendulum with magnet and reed switch which is referred to hereafter as a "reed switch", a vibration sensor, a gyroscopic sensor, or an accelerometer. Based upon current technology, the actuator is preferably a printed circuit board with a microprocessor providing program and data storage and program processing. The gait sensor, output element, and power supply are preferably connected directly to the printed circuit board of the actuator. An output speaker that produce a series of audible beeps based upon the actuator signal is preferred for the output element. Peripheral sensory output devices which are connected to the component case via an output jack or wireless interface allow for the utilization of peripheral sensory output devices such as a vibrator for use by hearing impaired or typical audio headphones. The power supply will preferably consist of a battery receptacle for one or more replaceable batteries or will consist of a battery pack with a charger jack mounted in the component case. Additional sensing means, actuator means, sensory output means and power supply means will be known to persons skilled in the art and undoubtedly further means will be developed in the future that could be deployed in the present invention.

An irregular gait includes a gait wherein the left step duration and the right step duration are significantly different, the left step impact force and the right step impact force are significantly different, or the left step form and the right step form are significantly different. The left step duration is the elapsed time between the time that the user's left foot attains the left step start position, which is the left step forward most position and also the left foot impact position, and the time that the user's left foot attains the left step rear position. The left foot attains the left step rear position at the time that the right foot attains the right step start position. Likewise, the right step duration is the elapsed time between the time that the user's right foot attains the right step start position, which is the right step forward most position and also the right foot impact position, and the time that the user's right foot attains the right step rear position. The left foot attains the left step rear position at the time that the right foot attains the right step start position and the right foot attains the right step rear position at the time that the left foot attains the left step start position.

The left step impact force experienced by the user as the heel of the left foot first impacts the ground at the left foot impact position can be compared to the right foot impact force as the right foot first impacts the ground at the right foot impact position as an indicia of gait irregularity. In the case of almost all users, the maximum impact force experienced by the user for each step will be as the heel impacts the ground at the forward most position. This is true whether the user is engaged in slowing walking, fast walking, jogging or running. Accordingly, a gait sensor that senses the left step impact force and the right step impact force, can also be used to determine the time duration for successive left steps and successive right steps.

An irregular gait form includes a gait wherein the left step rotation, which is the lateral angular hip or lower torso rotation to the right from the walk direction to the maximum right rotation position, and the right step rotation, which is the lateral angular hip or lower torso rotation to the left from the walk direction to the maximum left rotation position, are significantly different. Since the maximum right step rotation will correlate with the right foot being in the forward most position and the maximum left step rotation will correlate with the left foot being in the forward most position, a gait sensor that determines the magnitudes of the left step rotation and the right step rotation respectively can also be used to determine the time durations for successive left steps and right steps.

The type of gait sensor that is to be used for the present invention will depend upon the gait characteristic that is to be used for determining gait irregularity. The step phase that is most likely to trigger any of these sensors is the forward position of each step because that is a position where the foot movement changes direction, the position where maximum impact force is imparted to the user, and the position where maximum hip and lower torso rotation is experienced. Accordingly, for gait step duration, a reed switch, a vibration sensor, or an accelerometer can be used. If step impact force magnitude is the gait characteristic to be used, then a vibration sensor or an accelerometer sensor is preferable. If step form is to be utilized, then the inventor has found that a gyroscopic sensor is a preferred sensor.

Because of the self-contained feature of the present invention, i.e. the sensor or sensors being mounted in the component case with the other components, in order to ensure proper performance of the sensors, the gait therapy device needs to be firmly attached to the body, clothing or accessories of the user. This is needed in order to provide for the instantaneous transfer of forces, accelerations, vibrations and rotations from the body of the user to the component case and thus to the sensor or sensors mounted therein. In this regard, the component case is preferably equipped with a belt clip or other type of attachment clip because the user's belt, or waist band in the case of athletic wear, will ordinarily fit snugly to the body of the user. A mid-abdomen position or a mid-back position is preferable for placement of an embodiment of the present invention using a gyroscopic sensor as the neutral position of the gyroscopic sensor will align roughly with the walk direction.

The actuator receives successive or continuous sensor signals of gait data from the gait sensor which may simply be successive step start pulse signals in the case of a reed switch, a continuous vibration signal from a vibration sensor, a continuous acceleration signal from an accelerometer, and a continuous angular deviation signal from a gyroscopic sensor. The actuator then generates successive actuating signals which are determined as a function of the input sensor signals.

If step duration is the gait characteristic being utilized, then the actuator may produce a signal which is a function of the time duration between successive step starts. In the case of a step impact force signal, the actuator signal will be a function of successive step impact force signals. Likewise, for successive angular rotation signals, the actuator will produce an actuator signal which is a function of the successive angular rotation signals. Although actuator signals which are a direct function of the step duration, step impact force, or step angular rotation of the user can be used to drive the output element, because of the large variations in the sizes, ages and physical conditions of users, and the range of activities between slow walking and sprinting, the inventor prefers to have the actuator generate actuator signals which are a function of the ratio of the left step duration to the right step duration, the left step impact force to the right step impact force, or the left step rotation to the right step rotation.

Regardless of the type of sensor being used and therefore the type of signal being received by the actuator, the actuator signal is used to drive the output element. A speaker mounted in the component case is preferred with the successive actuator signals driving the speaker on a real time basis, based upon the sensor signals received from the gait sensor. A preferred sensory output is a series of audible beeps from the output speaker with the pitch varying as a function of the step duration, step impact force, or step angular rotation, depending upon the type of sensor used for the gait sensor. While a simple speaker producing an audible beep with a variable pitch is the output device preferred by the inventor, a number of other output element devices and other real-time output means could be used. This would include a light bar, an LCD digital display, and a headphone jack.

DETAILED DESCRIPTION

Figure 1:
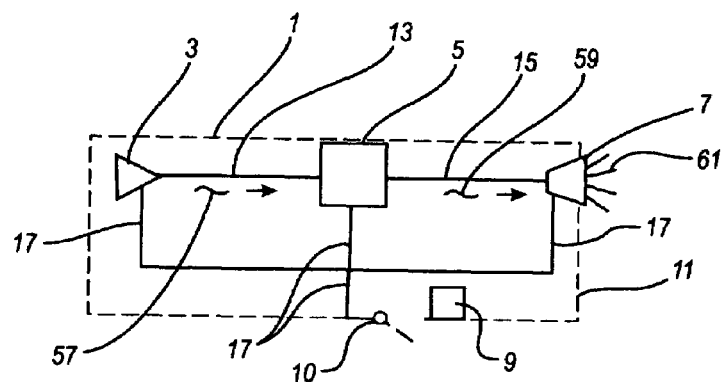
FIG. 1 is a schematic of a preferred embodiment of the gait therapy device of the present invention.

Referring first to FIG. 1 a block diagram schematic of a basic preferred embodiment of the gait therapy device 1 of the present invention is shown. This embodiment is comprised of a gait sensor 3, an actuator 5, an output element 7, a power supply 9 and a component case 11. The gait sensor is connected to the actuator by a sensor connection 13 and the output element is connected to the actuator by an output connection 15. The gait sensor, the actuator and the output element are each connected to the power supply by power connections 17. Based upon current technology, the actuator is preferably a printed circuit board with a microprocessor providing program and data storage and program processing. The gait sensor, output element, and power supply are preferably connected directly to the printed circuit board of the actuator, with the electronic and power connections being made through the printed circuit board of the actuator. Other actuator means and interconnecting means of interconnecting the components will be known to persons skilled in the art and technological advances will undoubtedly offer additional actuator means and interconnecting means for interconnecting the electronic and power components.

For some preferred embodiments the power supply will consist of a battery receptacle for one or more batteries or will consist of a battery pack. Preferred embodiments may also include a charger jack mounted in the component case to allow a charger to be connected to the power supply. For the preferred embodiment shown, the gait sensor, the actuator, and the output element are all operated on DC power, which for safety, convention, convenience and economy will preferably be no more than twelve volts. Of course, AC power could be used for one or more of these components but this would normally require a transformer, inverter or other device known in the art for converting DC voltage from the batteries to AC. As indicated above, the power supply can be as simple as a battery receptacle for one or more replaceable batteries or may consist of a battery pack with a charger jack built into the component case. Other power means will be known to persons skilled in the art and technological advances will undoubtedly result in additional power means being available for use with the present invention.

The gait sensor is preferably comprised of one or more sensing devices known to persons skilled in the art. The sensing devices that can be used include a weighted pendulum with magnet and reed switch which is referred to hereafter as a "reed switch", a vibration sensor, a gyroscopic sensor, or an accelerometer. Additional sensing means will be known to persons skilled in the art and undoubtedly further sensing means will be developed in the future that could be deployed in the present invention.

As indicated above, the present invention is primarily intended for self-use in gait therapy. However, it can be equipped with data storage and download capabilities for use by health care providers for evaluation and treatment. Regardless of the cause of gait irregularity, whether it be injury to one or more of the lower extremities or other parts of the body, medical intervention or other cause, an improper gait is generally undesirable and carries the potential for causing further medical problems, disabilities, decreased exercise and athletic performance, and chronic pain.

Figure 2:
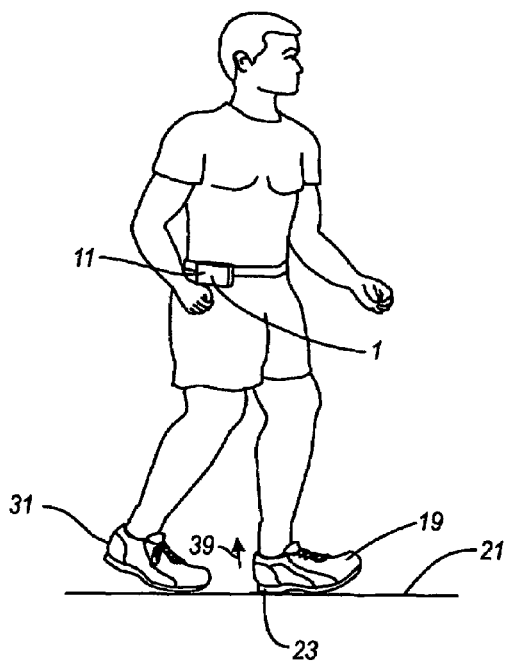
FIG. 2 is a side view perspective of a user wearing a preferred embodiment of the gait therapy device of the present invention and making a left step.
Figure 3:
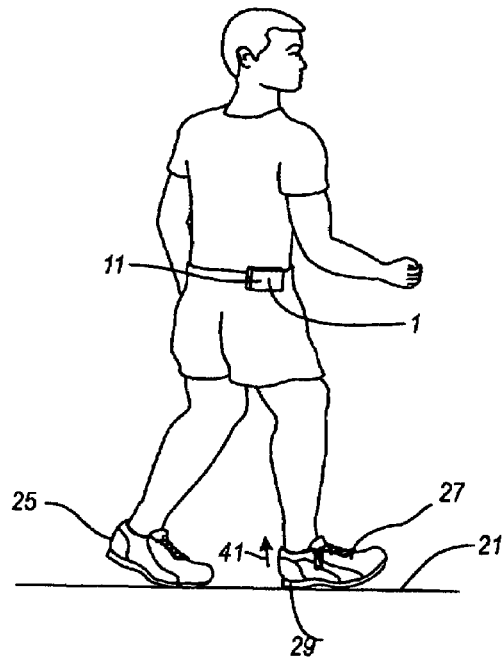
FIG. 3 is a side view perspective of a user wearing a preferred embodiment of the gait therapy device of the present invention and making a right step.

Referring now to FIG. 2 and FIG. 3, an irregular gait includes a gait wherein the left step duration and the right step duration are significantly different, the left step impact force and the right step impact force are significantly different, or the left step form and the right step form are significantly different. The left step duration is the elapsed time between the time that the user's left foot attains the left step start position 19, which is the left step forward most position and also the left foot impact position 23, and the time that the user's left foot attains the left step rear position 25. The left foot attains the left step rear position at the time that the right foot attains the right step start position 27. Likewise, the right step duration is the elapsed time between the time that the user's right foot attains the right step start position 27, which is the right step forward most position and also the right foot impact position 29, and the time that the user's right foot attains the right step rear position 31. The left foot attains the left step rear position at the time that the right foot attains the right step start position and the right foot attains the right step rear position at the time that the left foot attains the left step start position.

Referring again to FIG. 2 and FIG. 3, the left step impact force 39 experienced by the user as the heel of the left foot first impacts the ground at the left foot impact position 23 can be compared to the right foot impact force 41 as the right foot first impacts the ground at the right foot impact position 29 as an indicia of gait irregularity. In the case of almost all users, the maximum impact force experienced by the user for each step will be as the heel impacts the ground at the forward most position. This is true whether the user is engaged in slowing walking, fast walking, jogging or running. Accordingly, a gait sensor that senses the left step impact force and the right step impact force, can also be used to determine the time duration for successive left steps and successive right steps.

Figure 4:
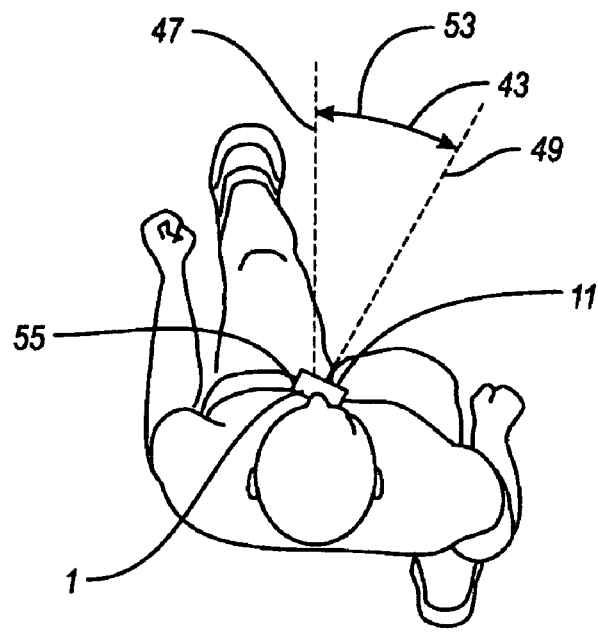
FIG. 4 is a top view perspective of a user wearing a preferred embodiment of the gait therapy device of the present invention and making a left step.
Figure 5:
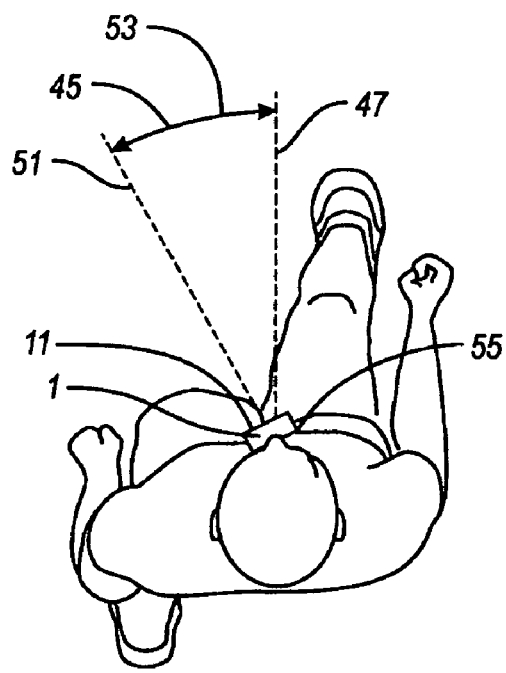
FIG. 5 is a top view perspective of a user wearing a preferred embodiment of the gait therapy device of the present invention and making a right step.

Referring now to FIG. 4 and FIG. 5, an illustration of an irregular gait form wherein the left step rotation 43, which is the lateral angular hip or lower torso rotation to the right from the walk direction 47 to the maximum right rotation position 49, and the right step rotation 45, which is the lateral angular hip or lower torso rotation to the left from the walk direction 47 to the maximum left rotation position 51, are significantly different. Since the maximum right step rotation will correlate with the right foot being in the forward most position and the maximum left step rotation will correlate with the left foot being in the forward most position, a gait sensor that determines the magnitudes of the left step rotation and the right step rotation respectively can also be used to determine the time durations for successive left steps and right steps.

The type of gait sensor that is to be used for the present invention will depend upon the gait characteristic that is to be used for determining gait irregularity. The step phase that is most likely to trigger any of these sensors is the forward position of each step because that is a position where the foot movement changes direction, the position where maximum impact force is imparted to the user, and the position where maximum hip and lower torso rotation is experienced. Accordingly, for gait step duration, a reed switch, a vibration sensor, or an accelerometer can be used.

Because of the self-contained feature of the present invention, i.e. the sensor or sensors being mounted in the component case with the other components, in order to ensure proper performance of the sensors, the gait therapy device needs to be firmly attached to the body, clothing or accessories of the user. This is needed in order to provide for the instantaneous transfer of forces, accelerations, vibrations and rotations from the body of the user to the component case and thus to the sensor or sensors mounted therein. In this regard, the component case is preferably equipped with an attachment clip such as a belt clip because the user's belt, or waist band in the case of athletic wear, will ordinarily fit snugly to the body of the user. Depending on the type of sensor used, the gait therapy device may be clipped to or placed in the pocket of the user, if the clothing item fits snugly to the body of the user.

If step impact force magnitude is the gait characteristic to be used, then a vibration sensor or an accelerometer sensor is preferable. These types of sensors will produce a continuous signal which is a function of the impact force experienced with each step. As indicated above, whether the user is slow walking, fast walking, jogging or running, the maximum left step impact force 39 felt by the body of the user will likely be at the moment that the heel of the left foot contacts the ground at the left foot impact position 23 when the left foot is at the left step forward position 19. Likewise, the maximum right step impact force 41 experienced by the body of the user will be at the moment that the heel of the right foot contacts the ground at the right foot impact position 29 when the right foot is at the right step forward position 27. Although the maximum impact point for each step may vary somewhat, an irregular gait will normally produce an asymmetry in the impact force experienced by the body of the user between the left step and the right step.

Referring now to FIG. 4 and FIG. 5, if the embodiment of the present invention is to utilize step form to detect gait irregularity, then the inventor has found that a gyroscopic sensor is a preferred sensor for the gait sensor. This type of sensor can be used to produce a continuous signal which is a function of the hip or lower torso angle of rotation 53. An irregular gait will typically result in a significant difference between the left step rotation 43 and the right step rotation 45. A mid-abdomen position 55 as shown in FIG. 4 and FIG. 5, or a mid-back position is preferable for placement of an embodiment of the present invention using a gyroscopic sensor as the neutral position of the gyroscopic sensor will align roughly with the walk direction 47.

Regardless of the type of sensor used to sense gait irregularity, for preferred embodiments of the present invention, the gait sensor, the actuator, the output element and the power supply are contained in a compact component case 11. This allows the gait therapy device simply to be clipped to the belt or clothing of the user and turned on, being immediately available for use.

The actuator 5, based upon the status of present technology, preferably comprises a printed circuit board with a microprocessor. However, other actuator means for receiving the analog or digital sensor signals and generating a real-time actuator signal which is a function of the gait data as described herein, will be known to persons skilled in the art. Also, further advances in technology will undoubtedly provide additional actuator means for incorporation in the gait therapy device of the present invention.

The actuator receives successive or continuous sensor signals 57 of gait data from the gait sensor which may simply be successive step start pulse signals in the case of a reed switch, a continuous vibration signal from a vibration sensor, a continuous acceleration signal from an accelerometer, and a continuous angular deviation signal from a gyroscopic sensor. If the gait sensor which is used outputs an analog signal, the actuator will include an analog-to-digital convertor for the input sensor signals to convert the analog signals to a digital signal for processing by the actuator. The actuator then generates successive actuating signals 59 which are determined as a function of the input sensor signals. If an analog signal is needed to drive the output element, the actuator will include a digital to analog converter for the actuator signal.

If step duration is the gait characteristic being utilized, then the actuator may produce a signal which is a function of the time duration between successive step starts. In the case of a step impact force signal, the actuator signal will be a function of successive step impact force signals. Likewise, for successive angular rotation signals, the actuator will produce an actuator signal which is a function of the successive angular rotation signals.

Regardless of the type of sensor being used and therefore the type of signal being received by the actuator, the actuator signal is used to drive the output element 7. For the preferred embodiment shown in FIG. 1, the output element is a speaker mounted in the component case and the successive actuator signals 59 drive the speaker on a real time basis, based upon the sensor signals received from the gait sensor. Depending on the type of speaker used, a digital to analog converter may be included in the actuator for the actuator signal to drive the speaker. The result is a sensory output 61 which, for the preferred embodiment shown in FIG. 1, is a series of audible beeps from the output speaker with the pitch varying as a function of the step duration, step impact force, or step angular rotation, depending upon the type of sensor used for the gait sensor. Although actuator signals which are a direct function of the step duration, step impact force, or step angular rotation of the user can be used to drive the output element, because of the large variations in the sizes, ages and physical conditions of users, and the range of activities between slow walking and sprinting, the inventor prefers to have the actuator generate actuator signals which are a function of the ratio of the left step duration to the right step duration, the left step impact force to the right step impact force, or the left step rotation to the right step rotation. This has an added benefit of allowing the use of a speaker with a smaller pitch range and allows the speaker to be operated in a more pleasing pitch range regardless of the user characteristics or the type of activity.

If a reed switch is used for the gait sensor, the sensor signal will ordinarily be one of two analog signals, with the change from one signal to the other being triggered by a brief connection made in the reed switch at the start of each successive step. The actuator sends a signal to the output element each time the reed switch connection is made, with the output speaker producing a beep upon the receipt of each actuator signal, with the pitch of the sound output being a function of the time duration between the present step start and the previous step start or a function of the ratio of the time duration between the present step start and the previous step start to the time duration between the previous step start and the step start for the step prior to the previous step start.

For preferred embodiments, the actuator includes a microprocessor programmed to generate the desired actuator signals from the sensor signals. The microprocessor will preferably be a computer chip connected to the gait sensor and the output element by a printed circuit board of the actuator. If step duration is to be used by the actuator, the actuator must include a timing circuit or other timing means known to persons skilled in the art.

If an accelerometer is used for the gait sensor, the sensor signal will comprise a continuous signal with maximum acceleration values being correlated with the respective maximum impact positions of successive steps. This continuous accelerometer output is transmitted as a continuous signal to the actuator with the actuator generating a digital actuator signal for each step which is a function of the maximum acceleration values for the step or the ratio of the maximum acceleration value for the step to the maximum acceleration value for the previous step. The actuator signal is transmitted to the output speaker or other output element and, if the output element comprises a speaker, a beep is emitted for each maximum impact sensor signal received by the actuator. For preferred embodiments, the pitch of the beep emitted by the speaker for each step is a function of the magnitude of the maximum accelerometer signal for the step or the ratio of the maximum accelerometer signal for the step to the maximum accelerometer signal for the previous step. Alternatively the actuator can include a timing means and the actuator signal for each step can be a function of the time duration between the maximum impact signal for the step and the maximum impact signal for the previous step, or a function of the ratio of the time duration of the step to the time duration of the previous step.

As an alternative to the accelerometer sensor, a vibration sensor can be used to determine the maximum impact point for each step, which will be the maximum vibration amplitude point for the step. As with an accelerometer, a vibration sensor sends a continuous signal which is a function of the amplitude and frequency of the vibration being detected. This continuous vibration sensor output is transmitted as a continuous signal to the actuator with the actuator generating an actuator signal for each step which is a function of the maximum vibration values for the step or the ratio of the maximum vibration value for the step to the maximum vibration value for the previous step. The actuator signal is transmitted to the output speaker or other output element and, if the output element comprises a speaker, a beep is emitted for each maximum impact sensor signal received by the actuator. For preferred embodiments, the pitch of the beep emitted by the speaker for each step is a function of the magnitude of the maximum vibration sensor signal for the step or the ratio of the maximum vibration sensor signal for the step to the maximum vibration sensor signal for the previous step. As with an accelerometer, alternatively the actuator can include a timing means and the actuator signal for each step can be a function of the time duration between the maximum impact signal for the step and the maximum impact signal for the previous step, or a function of the ratio of the time duration of the step to the time duration of the previous step.

If a gyroscopic sensor is used for the gait sensor to sense gait form irregularity, this type of sensor can be used to generate a signal which is a function of the angle of lateral rotation of the hips or lower torso. Referring to FIG. 4 and FIG. 5, the gait form irregularity which will be evident from a significant difference between the right step rotation 45 and the left step rotation 43. The actuator transmits an actuator signal to the output speaker or other output element producing, in the case of a speaker, a beep for each maximum left and maximum right rotation with the pitch of the beep being a function of the angular rotation or the time duration between the present maximum rotation and the previous maximum rotation. Alternatively, the actuator signal for each step can be a function of the ratio of the maximum rotation for the step to the maximum rotation of the previous step or the ratio of the time duration of the present step to the time duration of the previous step.

An accelerometer can also be used for the gait sensor for hip or lower torso rotation sensing. The accelerometer will be used to detect a change in direction of the lateral rotation of the hips or lower torso and will generate a signal proportional to the rotational acceleration for each step. Again, either the time duration between rotation direction changes or the magnitude of the acceleration for the left step rotation and the right step rotation can be used by the actuator to generate actuator signals to actuate the output element. Alternatively, the ratio of the maximum rotational acceleration for each step to the maximum rotational acceleration for the previous step or the ratio of the rotation duration for the present step to the rotation duration of the previous step can be used to generate the actuator signal for each step.

Depending upon the output element used, an analog actuator signal may be required. For those types of output devices, the actuator will include a digital-to-analog converter for the actuator signal.

While a simple speaker producing an audible beep with a variable pitch is the output device preferred by the inventor, a number of other output element devices and other real-time output means could be used. This would include a light bar, an LCD digital display, and a headphone jack.

The power supply can consist of a battery receptacle for one or more replaceable batteries. Alternatively, the power supply can be a battery pack with a built in recharge jack.

The simplest and most economical embodiments of the present invention would employ only one type of gait sensor. At the present time the reed switch and the vibration sensor are the most economical.

A basic embodiment of the present invention consists of a reed switch or vibration sensor, an actuator with a timing element, a speaker, and a battery receptacle for replaceable batteries, with all gains and sensitivity settings being preprogrammed. The device would be enclosed in a component case with an on/off switch and a belt clip. Other embodiments could utilize additional components and features including (a) different sensors as described above; (b) multiple sensors with mode selection; (c) rechargeable battery pack with recharger jack; (d) light bar; (e) LCD digital display; (f) download data port; (g) peripheral output jacks; (h) gain or sensitivity control input; (i) output volume control; and (j) control and mode selection input panel. Other optional components and features will known to persons skilled in the art and additional components and features will become known due to advances in technology.

The controls for the gait therapy device could be as simple as an on/off switch which can be a pressure switch, a toggle switch or other type known in the art. Embodiments with more features can be equipped with a control panel with pressure sensitive keys, an LCD display for control interaction, and sensory output peripheral device interfaces. Control interaction can include mode selection and gain or sensitivity selection. This can include jacks for wire connection or wireless interface known in the art for gait data output, gait target input, and peripheral sensory output. A power input jack for battery re-charging or direct peripheral power input could be used.

Peripheral sensory output devices which are connected to the component case via an output jack or wireless interface allow for the utilization of peripheral sensory output devices such as a vibrator for use by hearing impaired or typical audio headphones.

Regardless of the type of gait sensor used or the type of sensory output used to provide real time feedback to the user as he or she walks, jogs or runs, the present invention is intended to provide real time gait feedback to the user for the user to use in modifying his or her gait on a real time basis.

Other embodiments and other variations and modifications of the embodiments described above will be obvious to a person skilled in the art. Therefore, the foregoing is intended to be merely illustrative of the invention and the invention is limited only by the following claims and the doctrine of equivalents.

What is claimed is:

1. Self-contained, portable, real-time gait therapy device attachable to the body of a user or to clothing or accessories worn by the user for self-use by the user comprising:

a) gait sensor for sensing the impact or form of successive steps of the user;
b) real-time actuator in communication with the gait sensor for determining the real-time differences between left step and right step duration, left step and right step impact force, or left step and right step form;
c) output element in communication with the real-time actuator for providing a real-time output signal to the user based upon the real-time differences between left step and right step duration, left step and right step impact force, or left step and right step form;
d) one or more power supplies, the gait sensor, the real-time actuator, and the output element respectively being connected to one or more of the power supplies; and
e) component case attachable to the body of the user or to clothing or accessories worn by the user, the component case housing the gait sensor, the real-time actuator, the output element, and the power supplies.

2. Self-contained, real-time gait therapy device as recited in claim 1 wherein the gait sensor comprises a reed switch.

3. Self-contained, real-time gait therapy device as recited in claim 1 wherein the gait sensor comprises a vibration sensor.

4. Self-contained, real-time gait therapy device as recited in claim 1 wherein the gait sensor comprises an accelerometer.

5. Self-contained, real-time gait therapy device as recited in claim 1 wherein the gait sensor comprises a gyroscopic sensor.

6. Self-contained, real-time gait therapy device as recited in claim 1 wherein the actuator comprises a printed circuit board with a microprocessor for generating the actuator signal, the gait sensor and the output element being connected to the circuit board, the power supply being connected to the gait sensor, the actuator and the output element through the circuit board.

7. Self-contained, real-time gait therapy device as recited in claim 1 wherein the actuator further comprises a timing element.

8. Self-contained, real-time gait therapy device as recited in claim 1 wherein the output element comprises one or more speakers.

9. Self-contained, real-time gait therapy device as recited in claim 1 wherein the output element comprises an annunciator.

10. Self-contained, real-time gait therapy device as recited in claim 1 wherein the output element comprises a light bar.

11. Self-contained, real-time gait therapy device as recited in claim 1 wherein the output element comprises an LCD display.

12. Self-contained, real-time gait therapy device as recited in claim 1 wherein the output element comprises one or more output jacks.

13. Self-contained, real-time gait therapy device as recited in claim 1 further comprising data download means.

14. Self-contained, real-time gait therapy device as recited in claim 1 further comprising a data download port.

15. Self-contained, real-time gait therapy device as recited in claim 1 wherein the component case further comprises an attachment clip.

16. Self-contained, real-time gait therapy device as recited in claim 1 further comprising an attachment means for attaching the component case to the clothing, belt or body of the user.

17. Self-contained, real-time gait therapy device as recited in claim 1 wherein the power supply comprises a battery receptacle for one or more batteries.

18. Self-contained, real-time gait therapy device as recited in claim 1 wherein the power supply is a rechargeable battery pack with a recharge jack mounted in the component case.

19. Self-contained, real-time gait therapy device as recited in claim 1 wherein the actuator includes means for determining the step duration for successive left steps and successive right steps of the user and the actuator signal is a function of the step duration of the successive left steps and right steps.

20. Self-contained, real-time gait therapy device as recited in claim 1 wherein the actuator includes means for determining the step duration for successive left steps and successive right steps of the user and the actuator signal for each step is a function of the ratio of the step duration for the step to the step duration for the previous step.

21. Self-contained, real-time gait therapy device as recited in claim 1 wherein the actuator includes means for determining the step impact force for successive left steps and successive right steps of the user and the actuator signal for each step is a function of the step impact force for the step.

22. Self-contained, real-time gait therapy device as recited in claim 1 wherein the actuator includes means for determining the step impact force for successive left steps and successive right steps of the user and the actuator signal for each step is a function of the ratio of the step impact force for the step to the step impact force for the previous step.

23. Self-contained, real-time gait therapy device as recited in claim 1 wherein the actuator includes means for determining the step rotation for successive left steps and successive right steps of the user and the actuator signal for each step is a function of the step rotation for the step.

24. Self-contained, real-time gait therapy device as recited in claim 1 wherein the actuator includes means for determining the step rotation for successive left steps and successive right steps of the user and the actuator signal for each step is a function of the ratio of the step rotation for the step to the step rotation of the previous step.

25. Self-contained, portable, real-time gait therapy device attachable to the body of a user or to clothing or accessories worn by the user for self-use by the user comprising:
a) sensing means for generating a sensor signal of real-time left step and right step impact or left step and right step form data for the user;
b) actuator means for receiving the sensor signal from the sensing means and generating a real-time actuator signal which is a function of the real-time differences between left step and right step duration, left step and right step impact force, or left step and right step form;
c) output means for receiving the actuator signal and producing a real-time sensory output to the user from the actuator signal, the sensory output being a function of the real-time differences between left step and right step duration, left step and right step impact force, or left step and right step form of the user;
d) power supply means for the gait sensor, the output element and the actuator; and
e) component case attachable to the body of the user or to clothing or accessories worn by the user for housing the sensing means, the actuator means, the output means, and the power supply means.

* * * * *